United States Patent [19]

Szvoboda et al.

[11] Patent Number: 4,994,469
[45] Date of Patent: Feb. 19, 1991

[54] DIACLYL-SUBSTITUTED METHYLENE-2,2,4-TRIMETHYL-1,2-DIHYDROQUINOLINES AND A PROCESS FOR THE PREPARATION THEREOF

[75] Inventors: János Szvoboda; Tamás Rozsnyai, both of Budapest; József Szente, Kiskunlacháza; László Melovits, Budapest; Imre Ötvös, Budapest; Ilona Légrádi, Budapest; László Proházka, Budapest; Jeno Fekete, Budapest, all of Hungary

[73] Assignee: Material Vegyipari Kisszovetkezet, Budapest, Hungary

[21] Appl. No.: 301,887

[22] PCT Filed: Apr. 22, 1987

[86] PCT No.: PCT/HU88/00026
§ 371 Date: Dec. 16, 1988
§ 102(e) Date: Dec. 16, 1988

[87] PCT Pub. No.: WO88/08420
PCT Pub. Date: Nov. 3, 1988

[30] Foreign Application Priority Data

Apr. 22, 1987 [HU] Hungary .................. 1740/87
Apr. 11, 1988 [HU] Hungary .................. 1740/87

[51] Int. Cl.$^5$ .................. A61K 31/47; C07D 215/06; C07D 215/08; C07D 215/12
[52] U.S. Cl. .................. 514/314; 546/168; 546/172; 546/176
[58] Field of Search .................. 546/168, 172, 176; 514/314

[56] References Cited

U.S. PATENT DOCUMENTS

| | | | |
|---|---|---|---|
| 4,046,765 | 9/1977 | Bar et al. | 546/176 |
| 4,356,306 | 10/1982 | Bar et al. | 546/176 |
| 4,510,147 | 4/1985 | Bar et al. | 514/314 |

FOREIGN PATENT DOCUMENTS 2166953  5/1986  United Kingdom .......... 514/314

OTHER PUBLICATIONS

March, "Advanced Organic Chem.", Second Edition (McGraw-Hill Book Co.), pp. 498–499 (1977).

Primary Examiner—Mukund J. Shah
Assistant Examiner—E. C. Ward
Attorney, Agent, or Firm—Herbert Dubno; Jonathan Myers

[57] ABSTRACT

There are provided new compounds of the Formula I

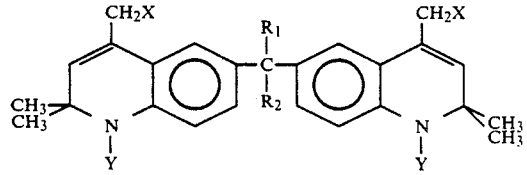

obtained by the condensation of 2,2,2-trimethyl-1,2-dihydroquinoline or salts thereof with an oxo derivative of the Formula $R_1R_2CO$—wherein $R_1$ stands for optionally substituted $C_{1-4}$ alkyl and
$R_2$ stands for optionally substituted $C_{1-2}$ alkyl,
X stands for hydrogen or $SO_3M$—wherein M stands for hydrogen, alkali or alkaline earth metal ion,
Y stands for hydrogen or acyl. The new compounds can be used as antioxidants, and particularly for increasing coccidiostatic effect.

9 Claims, No Drawings

DIACLYL-SUBSTITUTED METHYLENE-2,2,4-TRIMETHYL-1,2-DIHYDROQUINOLINES AND A PROCESS FOR THE PREPARATION THEREOF

CROSS REFERENCE TO RELATED APPLICATIONS

This application is a National Phase application of PCT/HU 88/00026, filed April 22, 1988 as based upon a Hungarian national application 1740/87, filed April 22, 1987 under the International Convention and to a modification thereof filed Nov. 11, 1988 also under the International Convention.

FIELD OF THE INVENTION

The present invention relates to new condensation products of 2,2,4-trimethyl-1,2-dihydroquinoline with oxo compounds and the derivatives of same as well as to a process for the preparation thereof and fodders and fodder premixes containing said compounds as well as pharmaceutical compositions containing as active ingredient the new compounds.

BACKGROUND OF THE INVENTION

In the last decades the significance of the use of antioxidants has increased all over the world in various fields and consequently, the use of the antioxidants has been widespread. Antioxidants ar most often used in the rubber industry and in the plastic industry and in this field the highest requirement is the specific effectivity of the antioxidants and in addition a very important factor is compatibility as well as low tendency to migration etc. The use of antioxidants in agriculture, in the food industry and recently in veterinary science and human therapy has increased significantly. While in the rubber and plastic industry several amine and phenol type antioxidants are used, for the stabilization of fodders, practically only 6-ethoxy-1,2-dihydro-2,2,4-trimethyl-quinoline (EMQ) and 2,6-di-tertiary butyl-hydroxytoluene (BHT) have been used. The antioxidants suitable for the stabilization of fodder mixtures have to meet simultaneously several essential requirements, such as broad spectrum, low toxicity, and freedom from injurious effects. The last point of view is considered in the recommendation of WHO/FAO Nutrition Meeting Ser. No. 40 A, B, C, WHO/FOD AU 67.29, according to which such antioxidants should be used for the mentioned purposes, which have $LD_{50}$ values exceeding 5 g/kg body weight. it is known that neither EMQ nor BHT meets this requirement. In spite of this fact these two compounds have been most accepted according to the present state of the art. These two compounds are the best in meeting said complex requirements.

6,6-methylene-bis(2,2,4-trimethyl-1,2-dihydroquinoline) is used in human therapy due to its radiosensitizing properties and it has proven not to be truly suitable for the stabilization of fodders because the extreme sensitivity of its methylene group very often results in coloration in the fatty tissue of the animals.

The antioxidant activity of 6,6'-ethylidene-bis(2,2,4-trimethyl-1,2-dihydroquinoline) called as XAX-M is suitable, its toxicity is low, but upon oxidation the ethylidene group is also oxidized and has a certain coloring effect.

A further disadvantage of XAX-M prepared according to Hungarian patent specification No. 162,358 is that the product is not homogeneous chemically, but according to page 4 of the Hungarian patent specification the polycondensation degree,i.e. the number of dihydroquinoline units changes depending upon the reaction conditions. The products obtained by acetaldehyde or by higher aldehyde condensation form a mixture of condensed molecules containing 2 to 4 dihydroquinoline units. A constant composition cannot be easily ensured, although this is required by the user.

No economic and practical process has been found so far. DOS 35 40 105 relates to the same product and to its property of increasing the coccidiostatic activity of known coccidiostatics.

OBJECT OF THE INVENTION

The object of the present invention is to provide new compounds having the good antioxidant activity of the known dihydroquinoline derivatives, but simultaneously to obtain a new product of chemically homogeneous structure suitable for human and veterinary use increasing the activity of coccidiostatics and with low toxicity. The new compounds should be able to be prepared by an economic technology in high purity.

DESCRIPTION OF THE INVENTION

We have now found that new compounds meeting the above requirements can be prepared if 2,2,4-trimethyl-1,2-dihydroquinoline is condensed under special reaction conditions with lower ketones and if desired the obtained compounds are sulfonated and/or acylated.

According to the present invention new compounds of the Formula (I)

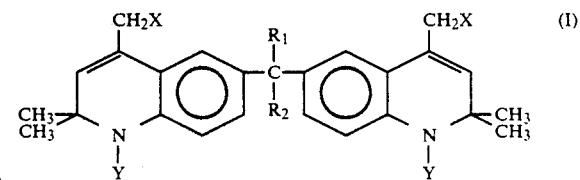

and acid addition salts thereof are prepared—wherein
$R_1$ stands for optionally substituted $C_{1-4}$ alkyl and
$R_2$ stands for optionally substituted $C_{1-2}$ alkyl,
X stands for hydrogen or $SO_3M$—wherein
M stands for hydrogen, alkali or alkaline earth metal ion, and
Y stands for hydrogen or acyl.

The new compounds can be prepared by condensing acetoanil (2,2,4-trimethyl-1,2-dihydroquinoline) or salts thereof with an oxo derivative of the Formula $R_1R_2CO$—wherein $R_1$ and $R_2$ are as defined above. in the presence of 1-5 %, preferably 2-3 % nitrogen containing base as a cocatalyst, preferably triethanol amine, pyridine or aniline and in the presence of a mineral acid, preferably 0.9-2.5 mole, preferably 1.25-1.75 mole hydrochloric acid as a catalyst relative to the dihydroquinoline in a solvent and, if desired, converting the obtained product to its acid addition salt or setting free the free base from the salt and, if desired, sulfonating and/or acylating the obtained base with sulfuric acid or oleum.

The acid addition salts can be formed with an acid, such as hydrochloric acid, hydrogen bromide or sulfuric acid, preferably hydrochloric acid.

In the meaning of $R_1$ the alkyl groups can be straight or branched and can stand for an optionally substituted $C_{1-4}$ alkyl, preferably methyl, ethyl, n-propyl,isopropyl, n-butyl, isobutyl, sec.butyl, preferably methyl, ethyl or isobutyl. The substituents can be selected from hydroxyl, halogen, $C_{1-4}$ alkoxy, carboxyl and $C_{1-4}$ alkoxycarbonyl. $R_2$ may preferably stand for $C_{1-2}$ alkyl, preferably methyl, ethyl, which can be substituted with the same groups as given for $R_1$. X preferably stands for hydrogen or $SO_3M$ wherein M stands for alkali or alkaline earth metal ion, preferably sodium, potassium or calcium ion. Y preferably stands for hydrogen or an acyl group, preferably acetyl, formyl, benzoyl, particularly acetyl.

Surprisingly the use of a nitrogen-containing base results in a quick condensation and thus the formation of by-products is eliminated.

In the course of condensation the reaction medium is the ketone itself in an amount of 0-40 % containing preferably 10-20 % of water.

Sulfonation can be carried out by methods known per se using oleum or sulfuric acid. Acylation can be performed with known acylating agents such as acetic anhydride, acetyl chloride, benzoyl chloride, formyl chloride.

The reaction mixture can be worked up by filtering the salt, preferably the hydrochloride and by centrifuging and converting it into the free base. A product of a purity higher than 95 % is obtained. According to another method the product is worked up together with the mother liquor, whereafter the unreacted starting material is distilled off in vacuo and thus a product of 60-80 % purity is obtained. A pure product is obtained without crystallization. The reaction is carried out at a temperature ranging from room temperature to the boiling point of the mixture, optionally under pressure.

As a ketone preferably acetone, methyl ethyl ketone or methyl isobutyl ketone, particularly acetone is used. The molar ratio of the reactant relative to acetoanil generally ranges from 0.5 mole to a several fold excess. Preferably a 10 fold excess, is used.

The other starting material used according to the invention is 2,2,4-trimethyl-1,2-dihydroquinoline and the compound is known from Bayer, J. Prakt. Chem. 2/33, 401/1886, and Combes, Bull. Soc. Chim. Fr. 49, 89 (1888).

The ketone condensation products of the invention are novel compounds. Due to their chemical structure they do not show a colorizing effect and can be used in a wide spectrum as antioxidant in the field of industry, food industry and fodder industry as well as in the field of therapy and veterinary science. The property of the new compounds by which they increase the activity of known coccidiostatics is particularly significant.

We have found for instance that 2,2-di(2',2',4'-trimethyl-1',2'-dihydroquinolin-6'-yl)-propane shows an excellent rubber antiageing activity and does not cause coloration. Similarly 2,2-di(2',2',4'-trimethyl-1',2'-dihydroquinoline)-butane can be used as a non-colorizing rubber antiageing agent as it is dissolved extremely well in rubber mixtures and it can be administered even at 5 % to products which are intended to contact with food.

2,2-di(2',2'-dimethyl-4'-sodium-methane sulfonate-1',2'-dihydroquinolin-6'-yl)-propane is highly soluble in water and can be consequently successfully applied in the form of injection in human therapy. The compound prevents the organism from detrimental free radical reactions. This is significant in the case of poisoning, radiation injuries and disturbances of the circulation. In veterinary therapy encephalomalacia in poultry-keeping can be treated when the compound is administered to the drinking water.

Out of the tested new antioxidant active ingredients the toxicity of 2,2-di(2',2',4'-trimethyl-1,2',2'-dihydroquinoline)-propane is very low and it can be satisfactorily applied for foddering, and food industrial and therapeutical purposes and for stabilizing organisms, as well as in animal fodders, especially as antioxidants in poultry, rabbit and pig fodders and as activity increasing components of coccidiostatics. Even under extreme conditions (in the presence of iron, copper compounds or halides) no decolorization occurs in the nutrient or in fatty tissues.

SPECIFIC EXAMPLES

In order to prove the coccidiostatic activity increasing effect of the compound according to Example 3 it was compared with Salinomycin ® and Monensin ®. The extent of infection of the animals was evaluated by 0, 1, 2, 3 crosses (+, ++, +++). The oocysta index consists of the sum of the crosses related to the total number of the animals.

TABLE 1

| Diet | | Oocysta Index | Death | Body Weight | Standard Deviation |
|---|---|---|---|---|---|
| Infected Control | | 30/10 | 2 | 145 | 41 |
| Compound according to Example 3 | 0 ppm | 10/10 | — | 165 | 31 |
| Salinomicin Compound according to Example 3 | 60 ppm 0 ppm | 30/10 | 3 | 141 | 27 |
| Salinomicin Compound according to Example 3 | 30 ppm 120 ppm | 0/10 | — | 126 | 20 |
| Salinomicin Compound according to Example 3, | 30 ppm 120 ppm | 0/10 | — | 141 | 20 |
| Salinomicin Compound according to Example 3 | 15 ppm 120 ppm | 0/10 | — | 144 | 25 |

The table shows that in case of Salinomycin ® the compound of Example 3 in a dose of 15 ppm gives the same protection, in case of Monensin the same compound at a dose of 30 ppm gives the same protection as the known compound administered per se at a dose recommended by the manufacturer.

The oocysta index is determined by a known method: the oocystas are counted microscopically. 25 visual fields are tested at the same time. If the number of the oocystas counted per field is below 1, then the value is marked by +, if it is between 1-10, it is marked by ++, above 10 the value is marked by +++.

Antioxidant activity On the basis of active oxygen method (ADM)

1. Description of the method

Under the thermostatic conditions a uniform stream of air is passed through the samples containing and not containing antioxidant. The change of Lea-number by time is measured.

2. Used materials

Glycerol trioleate purum $C_{57}H_{104}O_6$ LOBA FEINCHEMIE

K.J. p.a.

Chloroform
Glacial acetic acid
$Na_2S_2O_3$ 0.002 N solution
Starch indicator

3. Test method

Into 4 thermostated test cuvettes 30 g of glycerol trioleate are weighed in, in which 20 mg (0.02 %) test-antioxidant had been dissolved. The cuvettes are maintained at 70° C. and air is passed through the test oil at a velocity of 9.6–10 l/hour. A sample is taken every hour from the control and every 4 hours from the antioxidant samples and Lea-number is measured as follows:

To about 1 g of sample 30 ml of a solution of a 1:1 chloroform and glacial acetic acid and 1 g solid potassium iodide is added, it is boiled for 60 sec, rapidly cooled and 15 ml of 5 % aqueous potassium iodide solution is added.

It is titrated with 0.002 N $Na_2S_2O_3$ solution in the presence of a starch indicator.

$$\frac{(\text{Consumption/ml } 0.002 \text{ N } Na_2S_2O_3) - \text{blank test} \times \text{factor}}{\text{weighing in (g)}}$$

4. Results
4/1. control

| Time (h) | 1 | 2 | 3 | 4 | 5 | 6 | 7 | 8 | 9 | 10 | 11 | 12 |
|---|---|---|---|---|---|---|---|---|---|---|---|---|
| Lea number | 12.4 | 24.9 | 21.6 | 24.3 | 38.4 | 37.3 | 52.4 | 63.3 | 80.0 | 85.3 | 108 | 111 |

4/2. Samples

| Time (h) | 4 | 8 | 12 | 16 | 20 | 24 | 28 | 31 | 34 |
|---|---|---|---|---|---|---|---|---|---|
| MTDQ comparative 6,6'-methylene-bis-derivative (Melting point 156° C.) | 17.1 | 22.2 | 26.0 | 29.2 | 32.4 | 42.5 | 55.1 | 73.3 | 95.7 |
| 80% material according to Example 2 | 20.2 | 19.3 | 18.6 | 25.2 | 29.4 | 36.6 | 44.5 | 58.4 | 64.9 |
| 98% material according to Example 4 | 16.3 | 19.4 | 21.0 | 23.5 | 38.5 | 32.0 | 39.1 | 46.3 | 60.8 |
| acetyl derivative according to Example 7 | 16.9 | 23.2 | 27.8 | 33.0 | 42.6 | 69.2 | 103.5 | | |

In the case of $X = SO_3Na$ a water soluble antioxidant is obtained, which is tested in the following heterogeneous system:

30 ml water neutralized with 1 ml phosphate buffer of pH=7. 20 g glycerol trioleate, 1.5 g 30 % fatty alcohol sulphonate.

20 g of the tested antioxidant agent are added to the emulsion thus prepared. The weighing in of the antioxidant and the Lea numbers are related to the oil content.

| Lea number/time | 0 | 2 | 4 | 6 | 8 | 10 | 12 |
|---|---|---|---|---|---|---|---|
| Control | 2.8 | 6.6 | 9.0 | 26.9 | 72.9 | 124.1 | 267.3 |
| $SO^-_3Na^+$-derivative | 2.8 | 3.7 | 6.1 | 10.9 | 28.0 | 45.0 | 93.7 |
| Glutathion | 2.8 | 3.3 | 4.7 | 9.1 | 16.3 | 34.1 | 51.6 |
| L-ascorbic acid | 2.8 | 8.8 | 32.6 | 69.6 | 103.0 | 132.0 | 193.0 |

EXAMPLE 1

To a four necked flask equipped with a stirrer and a thermometer, a feeding funnel and reflux 150 parts by weight of acetone containing 10 % water, 105 parts by weight of acetoanil, 2.5 parts by weight of pyridine are added and 100 parts by weight of concentrated hydrochloric acid is added dropwise. The mixture is heated to the boiling point and stirred for 22 hours at this temperature. The mixture is cooled, whereafter 110 parts by weight of 40 % sodium hydroxide is added. The mixture is stirred under boiling, acetone is separated and 40 parts by eight of unreacted acetoanil are distilled off in vacuo. The bottom product is (60 parts by weight) of 2,2-di(2',2',4'-trimethyl-1',2'-dihydro-quinol-6'-yl)-propane of 80 % purity.

Melting point: 125–135° C.

EXAMPLE 2

To an autoclave which can be heated by steam and cooled by water and equipped with a thermometer, stirrer and a feeding opening 100 parts by weight of acetoanil, 2 parts by weight of triethanolamine, 280 parts by weight of anhydrous acetone and 106 parts by weight of concentrated hydrochloric acid are added. The equipment is closed and the content is stirred under pressure for 12 hours at 72–75° C., then it is cooled to 40° C. and neutralized by adding 100 parts by weight of 40 % sodium hydroxide solution. The aqueous layer is removed and from the organic layer acetone is removed, whereafter acetoanil is distilled off in vacuo. Yield: 62 parts by weight of 76 % 2',2-di(2',2',4'-trimethyl -1',2'-dihydro-quinol-6'-yl)-propane.

Melting point: 120–135° C.

EXAMPLE 3

From the antioxidant according to Example 1 and 2 a product is obtained in a good yield which can be recrystallized from benzene, then from isopropanol, which melts at 156° C., is completely white and the purity of which is 96 % according to HPLC chromatography. The product shows a biological activity similar to that of the product of purity 80 %. By evaporating the mother liquor an excellent rubber ageing inhibitor is obtained.

EXAMPLE 4

One may proceed according to Example 1 but acetone is replaced by methyl ethyl ketone. Yield: 45 parts by weight of 2,2-di(2',2',4'-trimethyl-1',2'-dihydro-quinol-6'-yl)-butane, purity: 55 %. After recrystallization from hexane followed by isopropanol a product of purity 96–97 % is obtained melting at 117–228° C. The product is an excellent antioxidant and its synergistic effect makes a 80 % saving possible when used together with coccidiostatics. From the mother liquor a non-colorizing antioxidant for the rubber industry can be obtained.

EXAMPLE 5

One may proceed as disclosed in Example 1 but as a ketone, methyl isobutyl ketone is used. Yield: 20 % 2,2-di(2',2',4'-trimethyl-1',2'-dihydro-quinol-6'-yl)-isohexane. Purity: 50 %, melting point after recrystallization: 120°–126° C. The product can be used like the product in Example 4.

EXAMPLE 6

100 parts by weight of a 96 % product according to Example 3 are dissolved in 400 parts by weight of 96 % sulfuric acid, whereafter the mixture is slowly heated to 80° C. and the reaction is performed for 2–3 hours at this temperature. The sulfonated product is added dropwise to a mixture of 1000 parts by weight of water and 1000 parts by weight of ice and the precipitated sulfonic acid is filtered. It is recrystallized from hot water in the form of free acid and then converted to the sodium salt. The thus obtained colorless crystalline product is dried to constant weight.

Yield: 105 parts by weight

Analysis of the product dried at 120° C.:

C 55.1 %(54.91); H (5.4 %(5.42); N 4.56 % (4.75; 0 16.34 %

(16.27) S 10.9 % (10.85); Na 7.7 % (7.8).

The product is suitable for therapeutical purposes.

EXAMPLE 7

The product of Example 3 is used. 100 parts by weight of this product are dissolved in 600 parts by weight of acetic anhydride and the solution is heated for 2 hours under reflux. Acetic acid and the excess of the anhydride are distilled off from the crude product and it is recrystallized from 600 parts by weight of hot acetone. Yield: 114 parts by weight, melting point: 120°–121° C., and the product is obtained in the form of pale yellow crystals.

We claim:

1. A compound of the Formula (I)

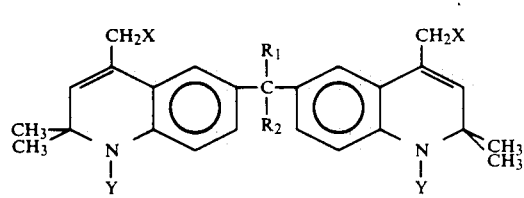

or a pharmaceutically acceptable salt thereof, wherein $R_1$ is $C_1$ to $C_4$ alkyl unsubstituted or substituted by hydroxyl, halogen, $C_1$ to $C_4$ alkoxy, carboxyl or $C_1$ to $C_4$ alkoxy-carbonyl;

$R_2$ is $C_1$ to $C_2$ alkyl unsubstituted or substituted by hydroxyl, halogen, $C_1$ to $C_4$ alkoxy, carboxyl or $C_1$ to $C_4$ alkoxy-carbonyl;

X is hydrogen or $SO_3M$ wherein

M is hydrogen, alkali metal or alkaline earth metal ion; and

Y is hydrogen, formyl, acetyl or benzoyl.

2. A compound of the Formula (I)

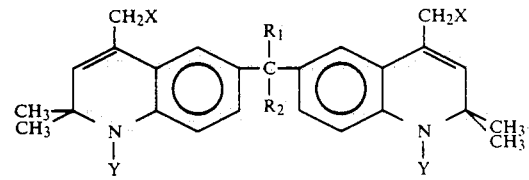

or a pharmaceutically acceptable salt thereof, wherein $R_1$ is $C_1$ to $C_4$ alkyl;

$R_2$ is $C_1$ to $C_2$ alkyl;

X is hydrogen or $-SO_3M$;

M is hydrogen, an alkali metal or alkaline earth metal ion; and

Y is hydrogen, formyl, acetyl or benzoyl.

3. A compound of the Formula (I)

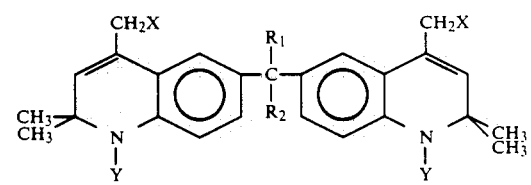

or a pharmaceutically acceptable salt thereof, wherein $R_1$ is $C_1$ to $C_4$ alkyl;

$R_2$ is $C_1$ to $C_2$ alkyl;

X is hydrogen; and

Y is hydrogen.

4. 2,2-di-(2',2',4', -trimethyl-1',2'-dihydro-quinol-6'-yl)-propane, or a pharmaceutically acceptable salt thereof as defined in claim 2.

5. 2,2-di-(2',2',4-trimethyl-1',2'-dihydroquinol-6'-butane, or a pharmaceutically acceptable salt thereof as defined in claim 2.

6. 2,2-di-(2',2',4'-trimethyl-1',2'-dihydro-quinol-6'-yl)-isohexane, or a pharmaceutically acceptable salt thereof as defined in claim 2.

7. The compound of the Formula (I) defined in claim 2 wherein $R_1$ and $R_2$ are each methyl, X is $-SO_3H$ and Y is hydrogen, or a pharmaceutically acceptable metal salt thereof.

8. The compound of the Formula (I) defined in claim 2 wherein $R_1$ and $R_2$ are each methyl, X is hydrogen and Y is acetyl, or a pharmaceutically acceptable salt thereof.

9. A pharmaceutical composition for treating a radiation injury which comprises a therapeutically effective amount of the compound of the Formula (I) as defined in claim 7, or a pharmaceutically acceptable salt thereof, in combination with a pharmaceutically acceptable inert carrier.

* * * * *

UNITED STATES PATENT AND TRADEMARK OFFICE
CERTIFICATE OF CORRECTION

PATENT NO. : 4,994,469

DATED : 19 February 1991

INVENTOR(S) : Janos SVOBODA et al.

It is certified that error appears in the above-identified patent and that said Letters Patent is hereby corrected as shown below:

Title Page:
In the heading of the patent, line [22] correct to read -- PCT Filed: Apr. 22, 1988 --.

Signed and Sealed this

Twenty-fifth Day of August, 1992

Attest:

DOUGLAS B. COMER

*Attesting Officer*   *Acting Commissioner of Patents and Trademarks*